United States Patent [19]

Treitinger et al.

[11] 4,338,281
[45] Jul. 6, 1982

[54] THIN FILM SEMICONDUCTOR GAS SENSOR HAVING AN INTEGRATED HEATING ELEMENT

[75] Inventors: Ludwig Treitinger, Munich; Peter Tischer, Strasslach; Brigitte Schneider-Gmelch, Munich, all of Fed. Rep. of Germany

[73] Assignee: Siemens Aktiengesellschaft, Berlin & Munich, Fed. Rep. of Germany

[21] Appl. No.: 254,855

[22] Filed: Apr. 16, 1981

[30] Foreign Application Priority Data

May 21, 1980 [DE] Fed. Rep. of Germany ....... 3019387

[51] Int. Cl.³ ............................................ G01N 27/04
[52] U.S. Cl. .................................... 422/98; 23/232 E; 73/27 R; 324/71 SN; 338/34
[58] Field of Search ........................ 422/98; 23/232 E; 324/71 N; 338/34; 73/23, 27 R

[56] References Cited

U.S. PATENT DOCUMENTS

| | | |
|---|---|---|
| 3,751,968 | 8/1973 | Loh et al. .......................... 422/98 X |
| 3,865,550 | 2/1975 | Bott et al. .......................... 22/232 E |
| 3,901,067 | 8/1975 | Boardman, Jr. et al. ......... 422/98 X |
| 4,045,178 | 8/1977 | Okinaka et al. ....................... 422/98 |

FOREIGN PATENT DOCUMENTS 2735222 2/1979 Fed. Rep. of Germany .
2933971 3/1981 Fed. Rep. of Germany .

*Primary Examiner*—Ronald E. Serwin
*Attorney, Agent, or Firm*—Hill, Van Santen, Steadman, Chiara & Simpson

[57] ABSTRACT

A thin film semiconductor gas sensor including a metal oxide semiconductor sensor layer whose electrical resistance changes in dependence upon the nature and concentration of a gas being detected and having a heating element integrated therewith is improved by forming the sensor from a semiconductor body having a shell zone located relatively close to an outer surface of such body and being doped to the point of degeneration, with two spaced apart metal contact strips being positioned on such doped shell zone for connection with a current source to heat the sensor.

9 Claims, 3 Drawing Figures

THIN FILM SEMICONDUCTOR GAS SENSOR HAVING AN INTEGRATED HEATING ELEMENT

BACKGROUND OF THE INVENTION

1. Field of the Invention

The invention relates to thin film gas sensors and somewhat more particularly to thin film semiconductor gas sensors having a metal oxide semiconductor sensor layer whose electrical resistance changes in dependence upon the nature and concentration of a gas being detected and having a heating element required for its function integrated into such sensor.

2. Prior Art

Selective gas sensors based on a metal oxide semiconductor are known, for example, from German Offenlegungsschrift No. 27 35 222. In this gas sensor, the metal oxide semiconductor comprises a layer of tin oxide ($SnO_2$) and detects the presence and concentration of ethyl alcohol in air. The operative principle of such gas sensor comprises the phenomena that with the absorption and reaction of a specific reactive gas from air, a change of electrical conductivity in the sensor layer occurs and is monitorable. The sensitivity of such a gas sensor is measured by the relative change of electrical conductivity per unit of gas concentration in air. This type of measuring arrangement is known from the above-referenced German Offenlegungsschrift No. 27 35 222.

Semiconductor gas sensors in the form of relatively thin films of metal oxide semiconductors, require, for their function, an elevated operating temperature, which, depending upon the construction of the sensor, its chemical composition and the medium to be detected, is at least 150° C. and preferably in the range of about 300° to 400° C.

U.S. Pat. No. 3,865,550 discloses a semiconductor gas sensor having a heating element in the form of a coiled filament fused into a glass bead. The metal oxide semiconductor sensor film is positioned on such glass bead.

The gas sensor disclosed in the earlier-referenced German Offenlegungsschrift No. 27 35 222, on the other hand, is provided with a coiled filament, for example, composed of a chromium-nickel wire, which is passed through a ceramic tube. The metal oxide semiconductor sensor film is applied on the exterior of this ceramic tube.

Other than the advantages that such coiled filaments are simply producable manually and are exchangeable as desired, these structural shapes have a series of disadvantages. For one thing, these types of structures are produceable only to a small extent automatically and thus require a large amount of manual labor, which is uneconomical. For another thing, such coil filaments, for the most part, are composed of platinum (because other metal heating wires are not as resistant to corrosion) and thus require a considerable outlay of noble metal.

German Offenlegungsschrift No. 29 33 971 (assigned to the instant assignee) discloses a gas sensor element which includes an insulating substrate of oxidized silicon, saphire or spinel having a heating layer composed of a vapor-deposited layer of nickel-chromium alloy or platinum on the substrate and a contact layer composed of platinum or gold/palladium vapor deposited on the nickel-chromium layer.

SUMMARY OF THE INVENTION

The invention provides thin film semiconductor gas sensor elements which are operable at elevated temperatures whereby rational structures can be produced with a minimum of manual labor and during the operation of which, a reliable and rapid indication and registration occurs.

In accordance with the principles of the invention, thin film gas sensors of the type earlier described are improved by forming the sensor carrier from a semiconductor body which has a shell zone located relatively close to an outer surface of such body (i.e., on or near an outer surface thereof) and which is highly doped, up to the point of degeneration, and which is provided with two spaced-apart metal contact strips for connection to a current source (i.e., for heating connection).

The invention was derived from the following considerations: In contrast to electrical resistance of metal heating wires or layers, the resistance of highly purified (non-degenerative) semiconductors decreases greatly with increasing temperatures. If a constant voltage is applied to a metal heating wire which is large enough to heat-up such wire, then the current applied to an alloy having an approximately constant resistance also remains constant so that the heating capacity remains constant. If the electrical resistance of a heating wire increases with temperature, as for example, with platinum, then the current decreases somewhat. Accordingly, on the whole, a stable operating temperature will result from an applied voltage and the characteristic resistance value of a select metal used in constructing a heating wire or layer. If on the other hand, a voltage is applied to highly purified semiconductor which is large enough to heat-up such semiconductor, then the electrical resistance of such semiconductor decreases greatly. In other words, the current rises steeply with constant voltage so that heating becomes even greater by application of a greatly increased current. However, such an increased current can destroy the semiconductor material due to a "thermal rupture" or breakdown. If, despite this, it is desirable to use a semiconductor as a heating element in this manner, then the applied voltage must be controlled. However, a control system requires a large additional outlay and is not economical.

By following the principles of the invention and providing a thin doped shell zone on or near the outer surface of the semiconductor body which is highly doped to such an extent that such an abnormality of the semiconductor occurs that the conductivity thereof attains an almost temperature-independent value. The surface resistance which arises is determined by the thickness of such doped zone and by the dopant concentration therein. In case of silicon, such a zone is preferably doped with phosphorous or boron. Such highly doped zones are utilized in semiconductor technology for attaining linear current-voltage characteristics at metal-semiconductor transitions.

An exemplary embodiment of the invention comprises a silicon body having a highly doped surface zone with a thickness of about 10 to 50 $\mu$m and a dopant concentration in the range of about $10^{24}$ to $10^{27}$ dopant atoms $m^{-3}$, with a metal oxide semiconductor layer, such as $SnO_2$, electrically separated from such doped zone, as by a $SiO_2$ layer, and two spaced-apart metal contact strips, preferably composed of platinum, positioned on the doped zone for a heating connection, i.e., for current input.

DESCRIPTION OF PREFERRED EMBODIMENTS

Figure 1:
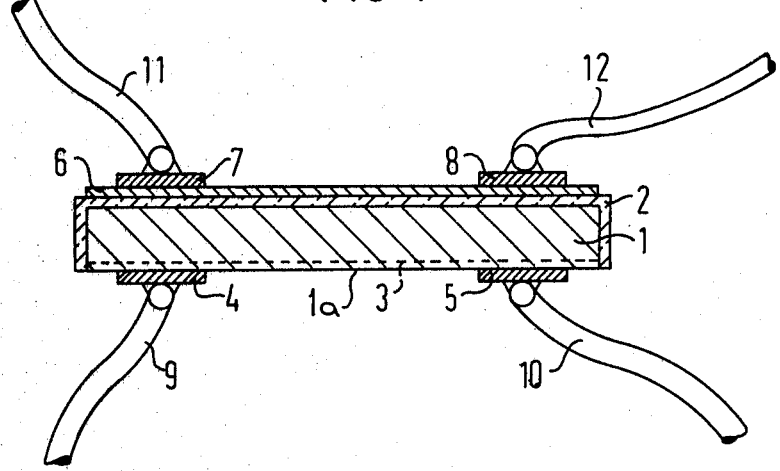
FIG. 1 is an elevated cross-sectional schematic view of an embodiment of the invention.

Referring now to the embodiment illustrated at FIG. 1, a semiconductor body 1, preferably composed of monocrystalline silicon and having a thickness of about 0.38 to 1 mm, is provided with an insulating $SiO_2$ layer 2 on all sides thereof, except side 1a, i.e., the underside in the illustrated arrangement. The insulating layer 2 has a thickness of at least equal to about 0.1 and not greater than about 1.0 μm. A highly doped n+ shell zone 3 is generated on the outer surface of side 1a, for example by diffusing dopant elements therein or by ion implantation, for example with a trivalent or pentavalent element, such as phosphorous. The doped shell zone 3 functions as a heating layer. As shown, zone 3 is provided with spaced-apart contact metal strips 5, preferably comprised of vapor-deposited platinum. A metal oxide semiconductor sensor layer 6, for example composed of tin oxide, is provided on an opposite side of body 1 away from zone 3 by sputtering or CVD (chemical vapor deposition) techniques. The metal oxide semiconductor layer 6 functions, at elevated temperatures, as a sensor for a select gas in air, for example, the exemplary $SnO_2$ layer functions as a sensor for ethyl alcohol vapors in air. Such metal oxide semiconductor layer is preferably about 50 nm thick and can be composed of select metal oxide semiconductors, such as the earlier mentioned tin oxide or platinum oxide or palladium oxide (sensors for carbon monoxide or hydrocarbons, respectively) or tin oxide having additions of niobium, vanadium, titanium and molybdenum (sensors for propane). Two spaced-apart metal contact strips 7 and 8 are vaporized on the sensor layer 6 as shown. Connection wires 9 and 10 are joined to the heating layer 3 via contact strips 4 and 5 and connection wires 11 and 12 are joined to the sensor layer 6 via contact strips 7 and 8. Connection wires 9 and 10 feed a current from a suitable source (not shown) to layer 3 for heating the same and wires 11 and 12 are connected to a resistance sensor (not shown) for determining any changes in electrical resistance in layer 6 upon the presence of a given gas in air. Preferably, the connection wires 9, 10, 11 and 12 have a diameter of about 25 to 100 μm and can be composed of a metal selected from the group consisting of platinum, gold, aluminum and nickel.

Figure 2:
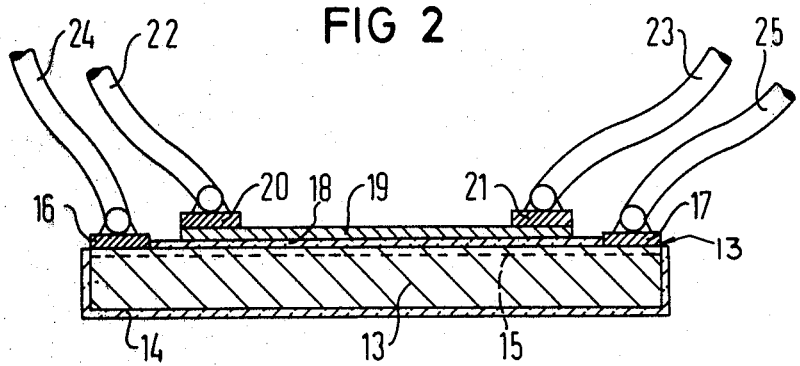
FIG. 2 is a substantially similar view of another embodiment of the invention.

Referring now to FIG. 2, a semiconductor substrate 13 having approximately the same dimensions as described for body 1 in FIG. 1, is provided with an insulating $SiO_2$ layer 14 on all surfaces thereof except surface 13a. A highly doped p+ shell zone 15 is generated on surface 13a by, for example, diffusing in boron atoms. Next, via suitable masking, a second $SiO_2$ layer 18 is generated on top of zone 15 via thermal oxidation. As shown, layer 18 terminates prior to the respective outer end regions of zone 15 and spaced-apart metal contact strips 16 and 17 are deposited on such outer end regions. A metal oxide semiconductor sensor layer 19, for example, composed of tin oxide, is deposited, for example, by sputtering or CVD techniques, over at least a substantial portion of the $SiO_2$ layer 18. Metal contact strips 20 and 21 are then positioned at opposite ends of the sensor layer 19. The heating contacts 16 and 17 are coupled to wires 24 and 25 for feeding a current to doped zone 15 so as to heat the same and sensor contacts 20 and 21 are coupled to wires 22 and 23 for monitoring a resistance of layer 19. With this arrangement, the heating layer 15 is located in the same side of substrate 13 as the sensor layer 19.

Figure 3:
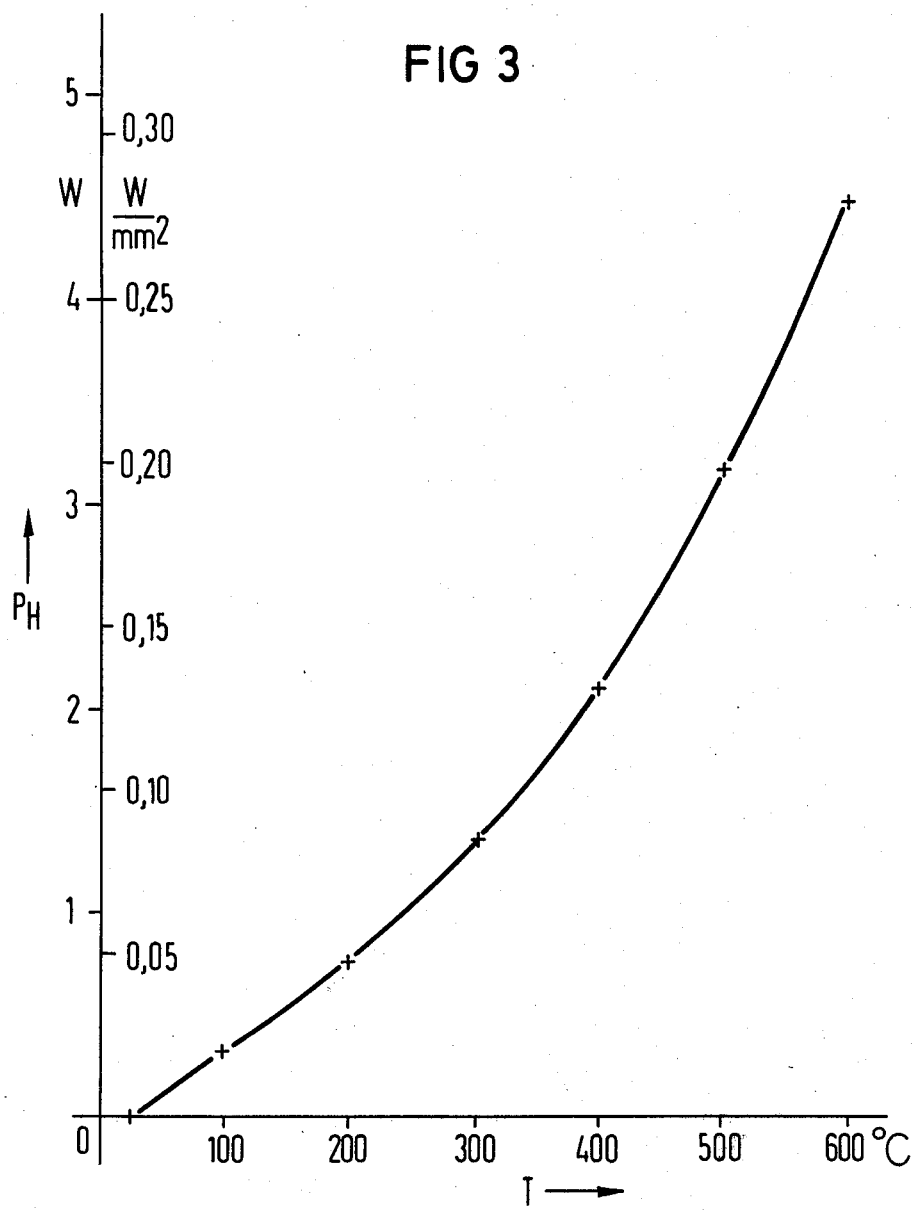
FIG. 3 is a graphical illustration showing the dependence of heating capacity, $P_H$, in watts for an exemplary 4 mm×4 mm sensor element constructed in accordance with the principles of the invention, relative to an operative temperature range in ° C.

In FIG. 3, on the ordinate, in addition to the $P_H$ value, the heating capacity value, $W/mm^2$, per sensor area is shown on the right-hand scale. The curve illustrated was generated with an arrangement identical in structure with that illustrated at FIG. 1. This measurement curve shows that heat transmission occurs on a relatively steep heat conduction path and thus provides a low energy consumption. For example, with about $0.125 \ W/mm^2$, an operating temperature of about 400° C. is attained.

The advantage which results from the principles of the invention, particularly the embodiments illustrated in FIGS. 1 and 2, relative to known sensor elements, are as follows:

All steps for producing sensor elements in accordance with the principles of the invention can be carried out with conventional silicon technology, that is, no additional assemblies are necessary and the arrangement can be produced via miniature construction techniques. Besides this, the heat transition with this type of arrangement occurs on a relatively short heat conduction path so that low energy consumption results. Thus, for example, the energy outlay for a sensor element as illustrated in FIGS. 1 and 2, at a temperature of about 400° C., is approximately 130 mW/mm (see FIG. 3). Accordingly, by following the principles of the invention, it is possible to produce gas sensors having an energy consumption of only approximately 100 mW.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

We claim as our invention:

1. In a thin film semiconductor gas sensor including a metal oxide semiconductor sensor layer wherein the electrical resistance of the metal oxide semiconductor layer changes in dependence upon the nature and concentration of a gas being detected, said sensor having a heating element required for its function integrated therewith; the improvement comprising wherein:

said sensor comprises a semiconductor body having a shell zone located relatively close to an outer surface of such body, said zone being highly doped to the point of degeneration and two metal contact strips positioned on said zone and apart from one another for a heating connection to said sensor.

2. In a thin film gas sensor as defined in claim 1 wherein said semiconductor body is composed of silicon and said shell zone is doped with a trivalent or pentavalent element.

3. In a thin film gas sensor as defined in claim 2 wherein said shell zone is doped with an element selected from the group consisting of boron and phosphorous.

4. In a thin film gas sensor as defined in claim 1 wherein said shell zone has a thickness in the range of about 10 to 50 μm.

5. In a thin film gas sensor as defined in claim 1 wherein said semiconductor body is composed of silicon and said doped shell zone is electrically separated from the metal oxide semiconductor sensor layer by an $SiO_2$ insulating layer.

6. In a thin film gas sensor as defined in claim 5 wherein said metal contact strips and said doped shell zone are located on a side of said silicon body which is away from said metal oxide semiconductor sensor layer.

7. In a thin film gas sensor as defined in claim 5 wherein said metal contact strips and said doped shell zone are located on the same side of said silicon body as said metal oxide semiconductor sensor layer.

8. In a thin film gas sensor as defined in claim 1 wherein said metal contact strips are composed of platinum.

9. In a thin film gas sensor as defined in claim 1 wherein said shell zone has a dopant concentration of about $10^{24}$ to $10^{27}$ dopant atoms $m^{-3}$.

* * * * *